(12) United States Patent
Iwatschenko

(10) Patent No.: US 7,594,577 B2
(45) Date of Patent: Sep. 29, 2009

(54) METHOD AND DEVICE FOR MOISTENING NON-BIOLOGICAL MEDICAL IMPLANT MATERIAL

(75) Inventor: Peter Iwatschenko, Neunkirchen (DE)

(73) Assignee: MTF MediTech Franken GmbH, Eckental (DE)

( * ) Notice: Subject to any disclaimer, the term of this patent is extended or adjusted under 35 U.S.C. 154(b) by 782 days.

(21) Appl. No.: 10/515,432

(22) PCT Filed: Jun. 4, 2003

(86) PCT No.: PCT/EP03/05877

§ 371 (c)(1),
(2), (4) Date: Nov. 22, 2004

(87) PCT Pub. No.: WO03/101334

PCT Pub. Date: Dec. 11, 2003

(65) Prior Publication Data

US 2006/0108239 A1 May 25, 2006

(30) Foreign Application Priority Data

Jun. 4, 2002 (EP) ................................. 02012508

(51) Int. Cl.
*A61B 17/06* (2006.01)
(52) U.S. Cl. ..................................... 206/438; 206/524.8
(58) Field of Classification Search ................. 206/63.5, 206/205, 210, 363, 538, 524.8, 828; 623/23.5, 623/23.56, 923

See application file for complete search history.

(56) References Cited

U.S. PATENT DOCUMENTS

| 4,321,781 | A |  | 3/1982 | Hall |
|---|---|---|---|---|
| 5,370,221 | A |  | 12/1994 | Magnusson et al. |
| 6,149,655 | A | * | 11/2000 | Constantz et al. ............. 606/94 |
| 6,286,670 | B1 | * | 9/2001 | Smith ...................... 206/524.8 |
| 6,648,133 | B1 | * | 11/2003 | Blaschke et al. ......... 206/524.8 |
| 7,198,150 | B1 | * | 4/2007 | Blaschke et al. ......... 206/524.8 |
| 2002/0117408 | A1 | * | 8/2002 | Solosko et al. .............. 206/210 |

FOREIGN PATENT DOCUMENTS

| DE | 297 05 993 U1 | 9/1998 |
|---|---|---|
| EP | 0 559 627 A2 | 9/1993 |
| EP | 0 928 612 A2 | 7/1999 |
| EP | 1 321 447 A1 | 6/2003 |
| EP | 1 325 713 A1 | 7/2003 |
| FR | 2 604 620 A1 | 4/1988 |
| FR | 2 702 661 A1 | 9/1994 |
| WO | WO 90/11066 A1 | 10/1990 |
| WO | WO 00/21489 A1 | 4/2000 |

(Continued)

OTHER PUBLICATIONS

Jianguo Li et al., High-strength aluminate cement produced by cold isostatic pressure, Journal of Materials Science, 2000, 5879-5883, v.35, Kluwer Academic Publishers.

*Primary Examiner*—Luan K Bui
(74) *Attorney, Agent, or Firm*—Robert R. Deleault, Esq.; Mesmer & Deleault, PLLC

(57) ABSTRACT

A method and a device for moistening a porous medical material (50) utilize evacuation of the material before moistening it with a liquid which is contained in a container (48) for communication with the material (50).

5 Claims, 3 Drawing Sheets

FOREIGN PATENT DOCUMENTS

Figures 2A, 2B, 2C, 2D:
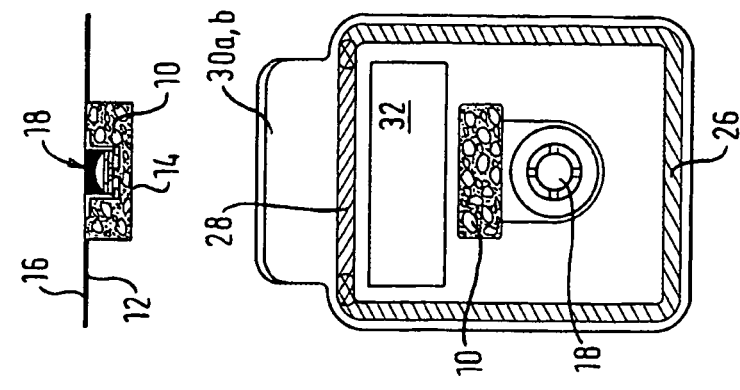

| | | |
|---|---|---|
| WO | WO 00/50102 A1 | 8/2000 |
| WO | WO 01/76534 A1 | 10/2001 |
| WO | WO 01/76535 A1 | 10/2001 |
| WO | WO 02/05750 A2 | 1/2002 |
| WO | WO 02/16209 A1 | 2/2002 |
| WO | WO 03/008285 A1 | 1/2003 |

* cited by examiner

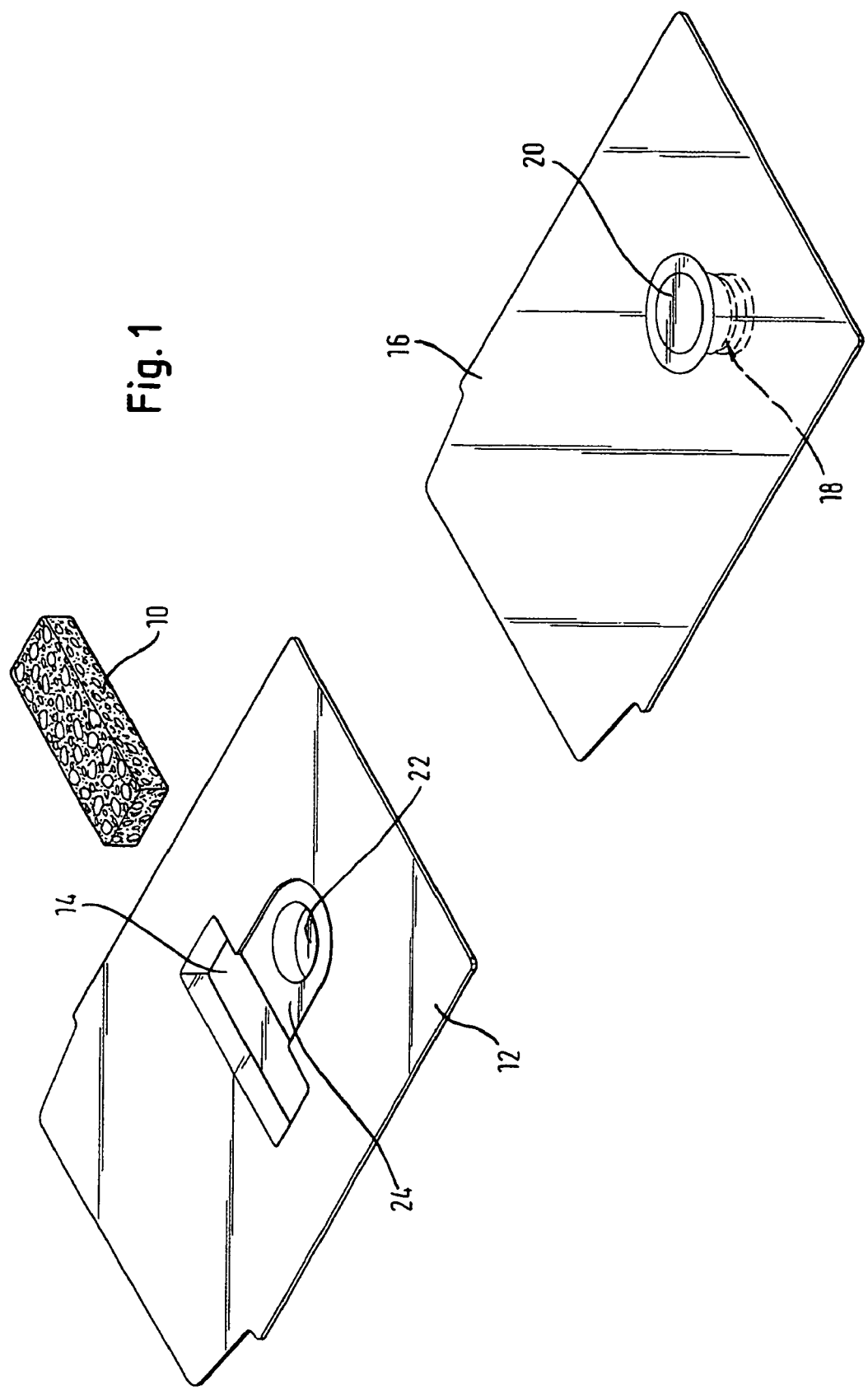

METHOD AND DEVICE FOR MOISTENING NON-BIOLOGICAL MEDICAL IMPLANT MATERIAL

The present invention is concerned with a method and an apparatus for moistening an essentially non-biological medical implant material.

A medical implant material, as this term is to be understood in the context of this invention, is a material to be inserted into the human or other mammal body and which material remains in that body for at least some time. A "non-biological" medical implant material is such a material having non-biological origin which means that the material is not obtained from another human being or mammal. In particular, dry materials, e.g. powders, for generating a ceramic medical implant material, are considered to be non-biological medical implant materials in the sense of the present invention. Such ceramic medical materials are, in particular, disclosed in the following Swedish priority applications SE 8900972-4, SE 9200303-7, SE 9803502-5, SE 0001322-7 and SE 0001321-9.

Recently, a chemically bound ceramic product was developed as a medical implant, in particular for filling dental cavities, cf. WO 01/76534 A1 and WO 01/76535 A1, and J. LI and L. HERMANSSON "High Strength Aluminate Cement Produced By Cold Isostatic Pressing", Journal of Materials Science 35 (2000) 5879-5883.

Also European patent applications EP 01 130 698.2 and EP 01 130 701.4 describe such ceramic materials.

The afore-mentioned prior art is, in the following, assumed to be known to the skilled reader.

In short, the new dental material is a chemically bonded ceramic material which is produced by reaction between a binding phase of one or more powdered binding agents and a liquid reacting with these bindings agents. A quantity of powder containing said binding phase is moistened (damped) with a liquid so that all powdered grains are brought into close contact with the liquid, whereupon the material is permitted to harden by reaction between said binding phase and the remaining liquid. The cited prior art also teaches to use one or more expansion-compensating additives, adapted to give the material dimensionally stable long-term properties.

These additives are mixed into said powder prior to or in conjunction with the moistening by the liquid. The cited prior art also teaches many details of how said ceramic material is chemically composed and prepared and these teachings can be applied in connection with the present invention.

In the prior art, the dry raw material is moistened (wetted) by exposing the dry raw material directly to a liquid, e.g. by pipetting the liquid directly onto the dry raw material. Excessive liquid which is not absorbed by the raw material is removed, e.g. wiped off. This technique has the disadvantage that the moistening (wetting) of the raw material is very often not perfectly homogenous. The prior art technique of directly exposing the dry raw material to the liquid was in particular problematic with powdered raw material and, therefore, the dry raw material was used in a compact form, e.g. in form of a pill or tablet or the like. Nevertheless, the afore-mentioned difficulties to obtain a homogenous moistening of the raw material without excessive liquid were hard to overcome even when using a raw compact.

The afore-mentioned (not pre-published) EP 01 130 698.2 improves the technology of moistening dry raw material by means of a porous body, like a sponge, which is brought into contact with said raw material such that liquid is transferred from said porous body into said raw material. This technique improves the compactness and homogeneity of the final implant material, e.g. the final dental cavity filling. In particular, the formation of cracks and micro cavities within the implant material is avoided or substantially reduced.

The present invention aims at further improving the medical implant in this regard. The present invention also aims at reducing the time needed for moistening the material and, furthermore, aims at reducing a possible surplus of liquid which is not used for moistening.

In order to solve these problems, the present invention teaches a method of moistening a non-biological medical implant material, said method comprising the step of evacuating said material before moistening it.

The present invention also teaches a device for moistening a non-biological medical implant material, said device comprising an evacuated chamber containing said material.

In other words, the present invention teaches a method and an apparatus according to which the moistening of the medical implant material is enhanced by a suction effect caused by a vacuum.

The moistening is promoted by said suction effect which produces a pressure drop which, in turn, pushes the liquid into the material. In addition to that suction effect the moistening can also be promoted by other effects, like the capillary effect. Typically, the medical implant material moistened in accordance with the present invention is porous and, therefore, capillary action also drives the liquid into and through the porous material. The suction effect, according to the present invention, however, has a considerable advantage regarding the time needed for the moistening and the homogeneity of the moistening, i.e. the totally uniform penetration of the liquid into the material. In the medical art, the moistening of an implant material is often called "rehydratisation" although the liquid is not necessarily water.

The present invention also allows for an exact dosing of the liquid such that the surplus or overflow, i.e. the amount of liquid not necessary for moistening the material, can be reduced substantially. Such overflowing or excess liquid, in the prior art, often caused trouble when handling the material.

According to a preferred embodiment of the invention, the material is evacuated some time before it is moistened. Therefore, the suction effect is directly generated by the vacuum in the pores of the material.

According to another embodiment of the invention, the suction effect can be generated by evacuating a cavity which can be connected to the material such that gas is transferred from the material into the evacuated cavity. If that connection is generated shortly before and/or during the moistening action and if the liquid is supplied at another location to the material, e.g. at the side opposing the gas-communicating connection, the liquid is sucked into and through the material and a homogenous moistening is obtained inside the material. According to this embodiment of the invention, the evacuation of the material takes place immediately before the moistening action.

According to a preferred embodiment of the invention an apparatus is provided comprising a container which can be evacuated and which comprises walls which are essentially stable under vacuum. The porous medical material to be moistened can be stored in that container, wherein the material is also evacuated.

According to another preferred embodiment of the invention, the device is realized by a so-called evacuated package.

According to another preferred embodiment of the device according to the present invention, there is provided a first chamber in which the material is contained and a second chamber in which the liquid is contained. If both chambers can be connected such that the liquid can be transferred from one chamber into the other. The vacuum causes, upon that connection, the liquid to be sucked into the material.

According to another preferred embodiment of the invention the device comprises a septum for injecting a liquid for at least partially moistening the material.

According to another preferred embodiment of the invention the liquid contains a medicament.

For example, the afore-mentioned septum may be used to inject a medicament.

It is also possible to combine the afore-mentioned "two-chamber-system" and the "septum" such that the device comprises two chambers with a first chamber in which the evacuated porous material is contained, and a second chamber containing the liquid, wherein, at an appropriate position, the septum is arranged through which, in addition to the liquid, a medicament can be injected such that upon moistening the medicament is homogenously distributed in the material together with the liquid. For example, the septum can be arranged such that the medicament can be injected into the liquid or into the flowing liquid.

In connection with the above described two-chamber-system comprising a connecting line for liquid transfer it is possible to normally interrupt said connecting line, e.g. by a membrane or the like. That membrane can be arranged and dimensioned such that it brakes under pressure. For example, if the apparatus is realized as an elastic vacuum package, the user may cause pressure in the chamber in which the liquid is contained and this pressure causes the membrane to brake (or open) such that the liquid is sucked in the direction of the material to be moistened. Instead of the membrane also a valve can be used for this purpose.

According to another preferred embodiment which is most preferably used in connection with a vacuum package, a cavity is provided downstream of the material, e.g. that cavity maybe formed by a sheath which is relatively stiff, as compared to the elasticity of the foil of the vacuum package, such that excessive liquid which remains after fully moistening the porous material, is sucked away from the material such that the amount of liquid actually delivered into the material corresponds exactly to the amount of liquid necessary for homogenously moistening the material. Therefore, no excessive liquid remains at the material, such excessive liquid may be troublesome during use of the material.

The material which is to be moistened in accordance with present invention, can be arranged in a cavity, e.g. a sheath. Such an arrangement of the material in a cavity which is open at least at one side, is, in particular, most preferred when the material as such after evacuation does not comprise sufficient form stability under atmospheric pressure. Such an arrangement of the material to be moistened in a cavity like a sheath is also very advantageous if the material is in powdered form. Such powder material can be arranged in sheath at least part of which is permeable by gas but not by the powder particles. If vacuum is applied outside the sheath, the inner cavity of the sheath can be evacuated together with the powder and, later, that evacuated powder can be moistened in accordance with the invention directly in that sheath.

Also a material to be moistened which has a stable configuration if evacuated and if exposed to atmospheric pressure can be advantageously be arranged in such a cavity, e.g. a sheath, because such an arrangement allows for a supply of liquid into the material at a well-defined position, e.g. at one end of a cylindrical sheath. Furthermore, that arrangement also promotes a complete and homogeneous moistening of the material. Overflowing liquid can easily be removed by means of the cavity, e.g. by a suction effect or simply by allowing the overflowing liquid to flow out of the cavity due to gravity action.

According to this invention, an essentially non-biological medical implant material is moistened. The term "essentially" refers to the fact that the non-biological material, e.g. the above-described ceramic material, may contain some biological material. For example, the non-biological material like the above-stated ceramic material may comprise a certain relatively small percentage of biological material distributed in the non-biological material. For example, Spongiasa can be distributed in the non-biological material. For example, some small percentage, e.g. up to 10% or 20%, biological material can be distributed in the non-biological material. Nevertheless, the medical implant material is still considered "essentially non-biological".

The liquid for moistening is, preferably, an electrolyte solution.

In the following, embodiments of the present invention are further detailed with reference to the drawings. In the drawings FIG. 1 shows a device for moistening a medical implant material, the device being separated into parts, FIGS. 2A, 2B, 2C and 2D show a device according to FIG. 1 in different stages of assembly, and FIG. 3 shows another embodiment of a device for moistening an absorbent material, said device comprising an evacuated package.

The devices shown in the figures are, in particular, suitable for moistening a ceramic material in accordance with the prior art mentioned above, i.e. a ceramic powder material, whether in pure powdered form or whether compacted in the form of a tablet or pill which is stable under atmospheric pressure.

For example, the material 10 to be moistened can have the porous shape as shown in FIG. 1.

The device for moistening the material 10 comprises a base 12, made e.g. from a transparent plastic material. In the embodiments shown in FIG. 1, the base 12 is made from a so-called blister material, which comprises some elasticity and nevertheless has sufficient stiffness in order to be stable in form even if an inner cavity is evacuated and the atmospheric pressure acts upon the surface.

The base 12 comprises a hollow depression or trough 14 into which the body of material 10 fits exactly. An upper member or cover 16 covers the trough 14 in gas-tight manner against the outer atmosphere. A septum 18, known as such, is also connected at the cover 16 in air-tight manner and protrudes in FIG. 1 downwards into a second trough 22 formed in the base 12. The septum 18 can be of known type and comprises a memberane 20 through which an injection needle (not shown) can be inserted. The terms "upwards" and "downwards" are here understood in the sense of the usual position of the device when in use.

The troughs 14 and 22 form, when the cover 16 is sealed on the base 12 (see below), a system of two chambers which are connected by a channel 24. In the embodiment shown in FIG. 1, the channel 24 has the shape of a relatively flat depression in the base 12.

FIGS. 2A to 2D show successive states of assembly of the device according to FIG. 1. FIGS. 2A to 2D show, below, a top view upon the base and the cover, respectively, and above a cross section perpendicular to the main plane of the base at the trough 22, wherein, additionally, the other trough 14 (which would not be included in the cross section) is shown.

Figure 3:
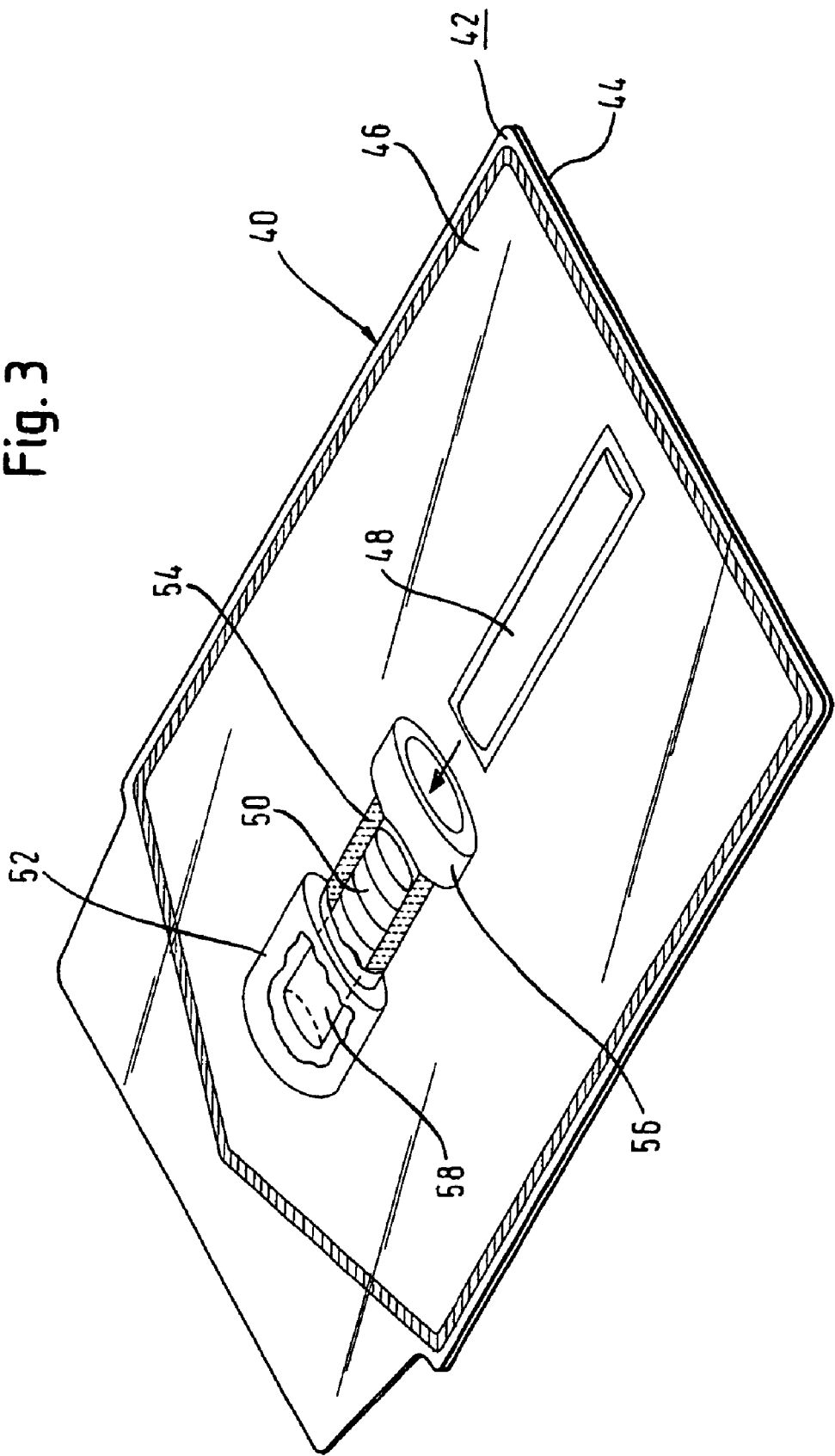

FIG. 2A shows the base 12 (blister) made from a transparent plastic foil of 0.2 to 0.4 mm strength. The dimensions of the troughs 14, 22 are adapted to the needs, i.e. the dimensions of the material 10 to be moistened and the septum 18, respectively.

FIG. 2B shows the cover 16 including the air-tight attached septum 18. The cover 16 may, e.g., be manufactured from a cover foil somewhat more elastic as compared to the base 12, the foil comprising a strength in the range of 0.1 to 0.2 mm.

FIG. 2C shows the base 12 and the cover 16 partly assembled. A welding stripe 26 seals the base and the cover partly wherein a certain area 25 is, at this stage, non-welded such that a vacuum pump (not shown) can evacuate the troughs 14, 22 through the open area 25. This way, the base and the cover are connected in surface contact and the material 10 positioned in trough 14 is also evacuated. Furthermore, trough 22, in which the septum 18 is received, is also evacuated, together with the septum, through channel 24 connecting troughs 14 and 22.

The base 12 and the cover 16 are sufficiently stable to allow the evacuation. Another embodiment comprising somewhat more elastic material like a vacuum package is described further below.

After evacuation, in the state according to FIG. 2C, another welding stripe 28 is e.g. thermally activated and the entire space between the base 12 and the cover 16 is evacuated except two pull-off edges 30a, 30b. Thus, the entire cavity between the base and the cover is sealed against the outer atmosphere in an air-tight manner.

A label 32 is applied at the cover 26 in order to give to the user information. For moistening the material 10 the user injects through the membrane 20 of the septum 20 a liquid, e.g. an electrolyte solution. A medicament can be added to the liquid. The size of the trough 22 is adapted to the size of the septum such that the liquid is directly transferred through the channel 24 into the trough 14 and, therefore, into the material 10. Since the trough 22 is adapted to the size of the septum and, furthermore, the size of the trough 14 is adapted to the size of the material 10, the user can supply exactly the amount of liquid necessary for moistening the material 10. For example, the amount of liquid necessary for completely and homogeneously moistening the material can be indicated to the user on the label 32.

The embodiment described above in connection with FIGS. 1 and 2 can be amended such that the foil used to cover the material can be fully elastical like a vacuum package. Such an embodiment comprising a vacuum package is shown in FIG. 3 schematically. The vacuum package 40 comprises a flat carrier 42 upon which two foils 44, 46 are laminated, one on top of the other. Between the foils 44, 46 a liquid reservoir 48 is formed like a cushion filled with the liquid for moistening the absorbent medical material 50. The material 50 is arranged in a sheath or cartridge 54 which is sufficiently stiff in order to protect the material 50 against forces from the outside like pressure. Preferably, the material of the cartridge 54 has sufficient form stability, however, also comprises some elasticity. A ring 56 at one opening of the cartridge 54 protects the sheath against squeezing. At the other end of the cartridge 54 a relatively stiff container 52 is provided for overflowing liquid. A pipe 58 protrudes into the container 52 such that overflowing excessive liquid is removed from the material 50.

For moistening the material 50, e.g. a porous body of the above type, the user presses the liquid container 48 (e.g. with the fingers) such that a well-defined point of fracture breaks. Said point of fracture is positioned at the arrow shown in FIG. 3 between the foils 44 and 46 such that the liquid from container 48 is transferred through the ring 56 into the inner cavity of the cartridge 54 and this way the moistening as explained above is performed. Due to a vacuum in the cavity in the cartridge 54 and in the container 52 the liquid penetrates into the material. Because of the vacuum in the container 52 a suction effect is also applied via the pipe 58 and overflowing excessive liquid is sucked into the container 52. This way, an exact control of the liquid for moistening is possible by adapting the volume of the container 52 and therefore, the suction action, to the material 50 to be moistened.

The embodiment shown in FIG. 3 can be amended such that between the elastic foils of the vacuum package 40 a septum can be arranged for injecting a liquid, similar to the embodiment described in connection with FIGS. 1 and 2.

As mentioned in the beginning, the invention can, in its most simple form, also be realized by a relatively stiff container in which the porous material to be moistened is arranged in an evacuated manner.

The devices and methods described above can be modified as follows:

Above, it was assumed that the gas which is evacuated from the porous material is air. However, according to an alternative embodiment of the invention, a protective gas can be used to fill temporarily the porous material. For example, an inert gas can be used, preferably however, a gas is used which can be dissolved in the liquid used to moisten the material. For example, $CO_2$ is a preferred gas used to fill more or less, the cavities in the porous material. $CO_2$ is very well soluble in many liquids used in medical applications, in particular, water. The use of a protective gas to fill the porous material has the advantage that during storage of the prepared material, the protection of the porous material is more effective. During storage, the protective gas is held in the chamber in which the porous material is contained, at a pressure which can be selected as follows:

If the pressure of the protective gas is smaller than the atmospheric pressure, there will be a suction effect regarding the liquid, when moistening the material.

If the pressure of the protective gas is selected larger than atmospheric pressure, the protective effect is enhanced.

If a pressure of the protective gas corresponding to the atmospheric pressure is selected, the filling of the gas into the porous material is eased.

The actual selection of the pressure will be made depending on the circumstances and the intended effect.

The afore-mentioned variants of the invention using a protective gas, can be combined with the above-described embodiments of the present invention illustrated in FIGS. 1 to 3. For example, the protective gas can be filled into the porous material in the factory manufacturing the device containing the material to be moistened later in a hospital or the like.

Also, the use of a protective gas can be combined with the above-described system in which a cavity is provided downstream of the material such that a vacuum can be applied to that cavity which is in fluid connection, at least temporarily with the chamber containing the porous material, such that excessive liquid and, at least partly, the protective gas is sucked away from the material such that both the excessive liquid and at least some protective gas is transferred away from the porous material into said cavity, such that the porous material is perfectly homogeneously moistened without any excessive liquid which may be troublesome during the is intended medical use of the material.

The invention claimed is:

1. A device for moistening an essentially non-biological medical implant material, said device comprising a chamber containing a non-biological medical implant material and means for moistening said material with a liquid, characterized in that an evacuated cavity is connected to said chamber containing the material wherein said evacuated cavity is adapted to suck away excessive liquid from said material moistened with said liquid into said cavity.

2. The device of claim 1 wherein said chamber has a septum for injecting said liquid to moisten said material.

3. The device of claim 1 wherein said material has a degree of compactness of 55-67 percent by volume solid phase.

4. The device of claim 1 wherein said material is a raw material comprising a binding phase of one or more binding agents which, after moistening with said liquid reacting with said one or more binding agents, forms first a formable material and then a chemically bonded ceramic material.

5. The device of claim 1 wherein said liquid includes a medicament.

* * * * *